US012268354B2

(12) United States Patent
Kitamura et al.

(10) Patent No.: US 12,268,354 B2
(45) Date of Patent: Apr. 8, 2025

(54) IMAGE RECORDING DEVICE, IMAGE RECORDING METHOD, AND RECORDING MEDIUM FOR RECORDING TIME-SERIES IMAGES OF ENDOSCOPY

(71) Applicant: OLYMPUS CORPORATION, Tokyo (JP)

(72) Inventors: Makoto Kitamura, Hachioji (JP); Yamato Kanda, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 748 days.

(21) Appl. No.: 17/395,696

(22) Filed: Aug. 6, 2021

(65) Prior Publication Data

US 2021/0361142 A1 Nov. 25, 2021

Related U.S. Application Data

(63) Continuation of application No. PCT/JP2019/005161, filed on Feb. 13, 2019.

(51) Int. Cl.
*A61B 1/00* (2006.01)
*A61B 1/005* (2006.01)
(Continued)

(52) U.S. Cl.
CPC .... *A61B 1/000094* (2022.02); *A61B 1/00006* (2013.01); *A61B 1/00071* (2013.01); (Continued)

(58) Field of Classification Search
CPC .......... A61B 1/000094; A61B 1/00006; A61B 1/00071; A61B 5/06; A61B 5/7267; (Continued)

(56) References Cited

U.S. PATENT DOCUMENTS 6,184,922 B1 2/2001 Saito et al.
9,743,824 B2 * 8/2017 Jia .................... A61B 1/000096
(Continued)

FOREIGN PATENT DOCUMENTS

CN 102340625 A 2/2012
JP H06-277178 A 10/1994
(Continued)

OTHER PUBLICATIONS

International Search Report dated Apr. 23, 2019 received in PCT/JP2019/005161.
English language only of WO 2005/001742 A2.

*Primary Examiner* — Mohamed A. Wasel
(74) *Attorney, Agent, or Firm* — Scully, Scott, Murphy & Presser, P.C.

(57) ABSTRACT

An image recording device includes a processor. The processor acquires time-series images of endoscopy, temporarily records all of the time-series images of the endoscopy in a buffer memory, retrieves the time-series images temporarily recorded in the buffer memory and identifies an appearance of a lesion from the retrieved time-series images, and records in a memory a predetermined image of the time-series images temporarily recorded in the buffer memory, according to the identified appearance of the lesion.

20 Claims, 7 Drawing Sheets

(51) Int. Cl.
*A61B 5/00* (2006.01)
*A61B 5/06* (2006.01)

(52) U.S. Cl.
CPC ................ *A61B 1/009* (2022.02); *A61B 5/06* (2013.01); *A61B 5/7267* (2013.01); *A61B 5/749* (2013.01)

(58) Field of Classification Search
CPC .......... A61B 5/749; G06T 2207/10068; G06T 2207/30096
See application file for complete search history.

(56) References Cited

U.S. PATENT DOCUMENTS 11,017,526 B2 * 5/2021 Angermann ......... G06V 10/776
2008/0303898 A1 * 12/2008 Nishimura ............. G16H 40/63 348/E7.085
2009/0287091 A1 * 11/2009 Son ...................... A61B 5/0084 600/478
2011/0301443 A1 * 12/2011 Yamaguchi ........ A61B 5/14551 600/324
2011/0301447 A1 * 12/2011 Park ...................... G06T 7/0016 600/407
2011/0319711 A1 * 12/2011 Yamaguchi .......... A61B 1/0655 600/109
2012/0014659 A1 1/2012 Hugosson
2012/0190922 A1 * 7/2012 Kaku .................. A61B 1/0005 600/109
2016/0242737 A1 * 8/2016 Zhou .................. A61B 1/00082
2019/0311474 A1 * 10/2019 Angermann ......... G06V 10/776

FOREIGN PATENT DOCUMENTS

JP H11-47085 A 2/1999
JP 2006-271870 A 10/2006
JP 2007-528746 A 10/2007
JP 2011-212094 A 10/2011
WO 2017/216922 A1 12/2017

* cited by examiner

IMAGE RECORDING DEVICE, IMAGE RECORDING METHOD, AND RECORDING MEDIUM FOR RECORDING TIME-SERIES IMAGES OF ENDOSCOPY

CROSS REFERENCE TO RELATED APPLICATION

This application is a continuation application of PCT/JP2019/005161 filed on Feb. 13, 2019, the entire contents of which are incorporated herein by this reference.

BACKGROUND OF THE INVENTION

1. Field of the Invention

The present invention relates to an image recording device, an image recording method, and a recording medium.

2. Description of the Related Art

For image diagnosis in the medical field, various systems have been developed which photograph medical images of various anatomical structures of individual patients in order to classify and evaluate disease states. As these photographing systems, for example, a CT (computed tomography) system, an MRI (magnetic resonance imaging) system, an X-ray systems, an ultrasound system, and a PET (positron emission tomography) system are known.

In Japanese Patent Application Laid Open Publication No. 2007-528746, a method has been disclosed for realizing a lesion detection function using so-called CADe (computer-aided detection/diagnosis) by machine learning of annotation data provided from a medical service worker, such as a doctor.

SUMMARY OF THE INVENTION

An image recording device according to an aspect of the present invention includes a processor. The processor is configured to acquire time-series images of endoscopy; temporarily record all of the time-series images of the endoscopy in a buffer memory; retrieve the time-series images temporarily recorded in the buffer memory, and identify an appearance of a lesion in the retrieved time-series images; and record in a memory a predetermined image of the time-series images temporarily recorded in the buffer memory, according to the identified appearance of the lesion.

An image recording method according to an aspect of the present invention includes: acquiring time-series images of endoscopy; temporarily recording all of the time-series images of the endoscopy; retrieving the temporarily recorded time-series images and identifying an appearance of a lesion in the retrieved time-series images; and recording a predetermined image of the temporarily recorded time-series images, according to the identified appearance of the lesion.

A non-transitory computer-readable recording medium on which an image recording program is recorded according to an aspect of the present invention causes a computer to execute a process for acquiring time-series images of endoscopy; a process for temporarily recording all of the time-series images of the endoscopy; a process for retrieving the temporarily recorded time-series images and identifying an appearance of a lesion in the retrieved time-series images; and a process for recording a predetermined image of the temporarily recorded time-series images, according to the identified appearance of the lesion.

DETAILED DESCRIPTION OF THE PREFERRED EMBODIMENTS

Hereinafter, embodiments of the present invention will be described with reference to the drawings.

First Embodiment

Figure 1:
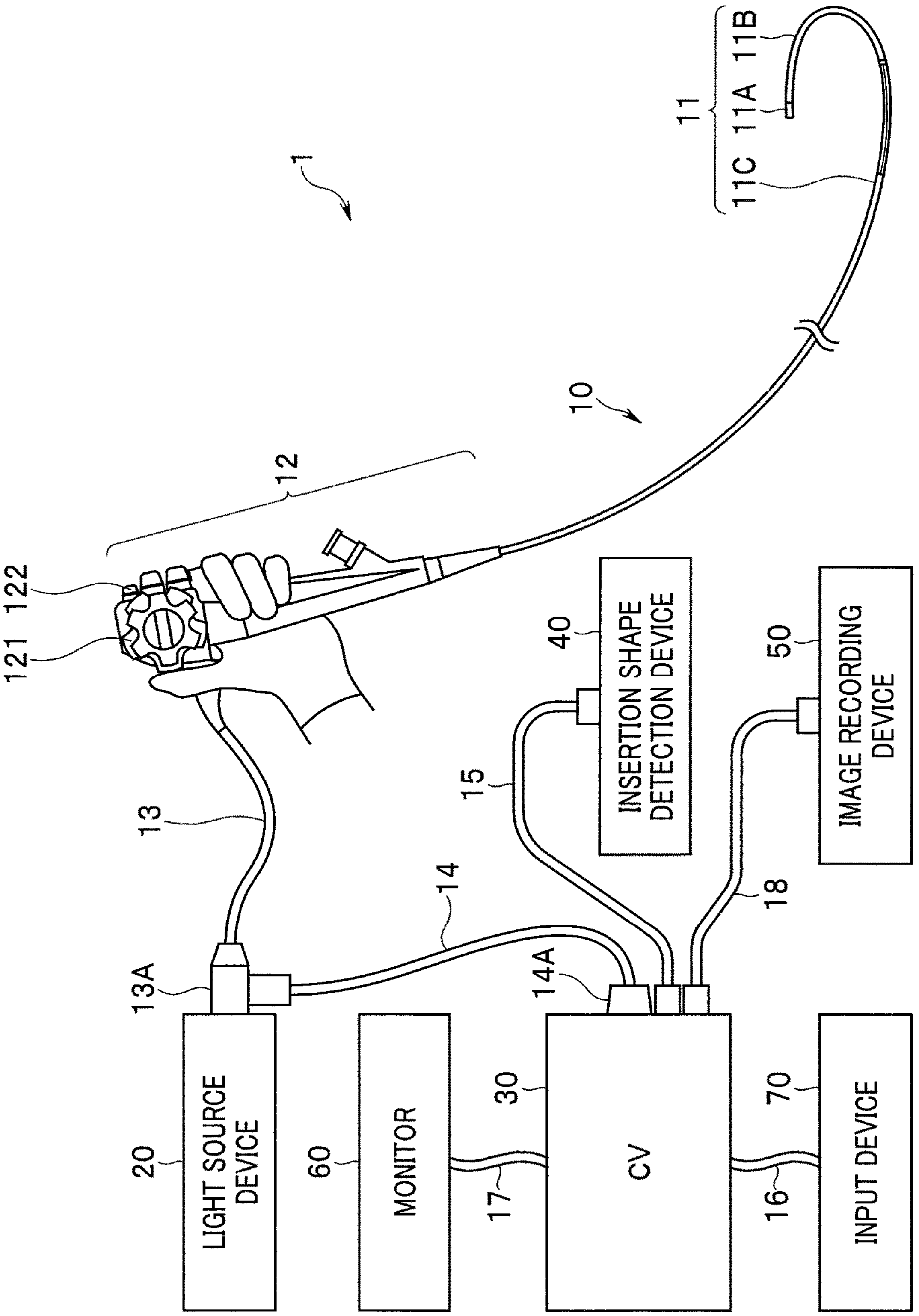
FIG. 1 is a block diagram showing a configuration of an endoscope system including an image recording device according to a first embodiment of the present invention.

FIG. 1 is a block diagram showing the configuration of an endoscope system including the image recording device according to a first embodiment of the present invention.

As shown in FIG. 1, an endoscope system 1 according to the present embodiment includes, for example, an endoscope 10, a light source device 20, a video processor 30, an insertion shape detection device 40, an image recording device 50, a display device 60, and an input device 70.

The endoscope 10 includes an insertion portion 11 to be inserted into a subject, an operation portion 12 provided on the proximal end side of the insertion portion 11, and a universal cord 13 extended from the operation portion 12. Further, the endoscope 10 is configured to be removably connected to the light source device 20 via a scope connector 13A provided at an end of the universal cord 13.

Further, the endoscope 10 is configured to be removably connected to the video processor 30 via an electrical connector 14A provided at an end of an electrical cable 14 extended from the scope connector 13A. Further, a light guide (not shown) for transmitting illumination light supplied from the light source device 20 is provided inside the insertion portion 11, the operation portion 12, and the universal cord 13.

The insertion portion 11 has flexibility and an elongated shape. In addition, the insertion portion 11 includes a hard distal end portion 11A, a bending portion 11B formed to be bendable, and an elongated flexible tube portion 11C having flexibility, which are arranged in this order from the distal end side.

The distal end portion 11A is provided with an illumination window (not shown) for emitting illumination light transmitted through the light guide provided inside the insertion portion 11 to a subject. In addition, the distal end portion 11A is provided with an image pickup unit configured to perform an operation according to an image pickup control signal supplied from the video processor 30, and to pick up an image of the subject illuminated by the illumination light emitted through the illumination window and output an image pickup signal. The image pickup unit includes an image sensor such as a CMOS image sensor or a CCD image sensor.

The operation portion 12 includes a shape that can be grasped and manipulated by a user. Further, the operation portion 12 is provided with an angle knob 121 configured to be able to perform an operation for bending the bending portion 11B in four directions, i.e., up, down, left, and right (UDLR) directions that intersect the longitudinal axis of the insertion portion 11. Further, the operation portion 12 is provided with at least one scope switch 122 capable of providing an instruction corresponding to an input operation of an operator (user), for example, an image-recording operation.

The angle knob 121 and the scope switch 122 in the operation portion 12 function as devices for inputting external information.

The light source device 20 includes, for example, at least one LED or at least one lump as a light source. Further, the light source device 20 is configured to be able to generate illumination light for illuminating the inside of a subject into which the insertion portion 11 is inserted and to supply the illumination light to the endoscope 10. Further, the light source device 20 is configured to be able to vary the amount of illumination light according to a system control signal supplied from the video processor 30.

The input device 70 is removably connected to the video processor 30 via a cable 16, and includes one or more input interfaces operated by the operator (user), such as a mouse, a keyboard, or a touch panel.

The input device 70 also functions as an external information input device for inputting a predetermined voice uttered by the operator. The input device 70 is configured to output to the video processor 30 an instruction corresponding to an operation or a voice input from the operator (user).

The insertion shape detection device 40 is removably connected to the video processor 30 via a cable 15. In the present embodiment, the insertion shape detection device 40 is configured to detect a magnetic field emitted from, for example, a source coil group provided in the insertion portion 11, and to acquire the position of each of a plurality of source coils included in the source coil group based on the strength of the detected magnetic field.

Further, the insertion shape detection device 40 is configured to calculate the insertion shape of the insertion portion 11 based on the positions of each of the plurality of source coils acquired as described above, and to generate insertion shape information indicating the calculated insertion shape and output the insertion shape information to the video processor 30.

Note that in the present embodiment, each part of the insertion shape detection device 40 may be configured as an electronic circuit, or may be configured as a circuit block in an integrated circuit such as an FPGA (field programmable gate array). In the present embodiment, for example, the insertion shape detection device 40 may be configured with one or more processors (such as a CPU).

The display device (monitor) 60 is removably connected to the video processor 30 via a cable 17, and includes, for example, a liquid crystal monitor. Further, the display device 60 is configured to display on a screen, for example, an endoscope image outputted from the video processor 30.

The image recording device 50 is removably connected to the video processor 30 via a cable 18. As described later in detail, the image recording device 50 includes an image acquisition unit configured to acquire time-series endoscopy images appropriately processed by the video processor 30, and also includes a recording unit configured to record the time-series endoscope images, and a lesion appearance identification unit configured to identify an appearance of a lesion from the acquired time-series endoscope images.

The video processor 30 includes an image processing unit configured to acquire image pickup signals outputted from the endoscope 10 and apply predetermined image processing to generate time-series endoscope images. Further, the video processor 30 is configured to perform a predetermined operation for displaying the generated endoscope image on the display device 60. Further, the video processor 30 is configured to generate and output various control signals for controlling operations of the endoscope 10, the light source device 20, the image recording device 50 and the like.

Further, video processor 30 is configured to perform an operation corresponding to an instruction from the input device 70 and the scope switch 122 of the operation portion 12, that is, an operation based on external information.

For example, when a predetermined voice (about discovery of a lesion, etc.) uttered by an operator is inputted through the input device 70 as described above, the video processor 30 transmits information corresponding to the voice input by the operator to a lesion appearance identification unit 52 in the image recording device 50, as notification information about the lesion discovery operation by the operator. The details will be described later.

Further, when the video processor 30 receives, for example, image-recording (release) operation information or still image generation (freeze) operation information from the scope switch 122 of the operation portion 12, the video processor 30 transmits the information corresponding to the operation by the operator to the lesion appearance identification unit 52 in the image recording device 50 as notification information about the lesion discovery operation by the operator, as with the above described case. The details will be described later.

Further, the video processor 30 is configured to control the driving state of the insertion portion 11 based on insertion shape information outputted from the insertion shape detection device 40, or the like.

Further, in the present embodiment, the video processor 30 is also configured to be able to grasp the state of the insertion portion 11 based on insertion shape information or the like outputted from the insertion shape detection device 40, for example, detect the movement speed and movement direction of the insertion portion 11 (e.g., the removal speed of the insertion portion), and perform determination about operation stop or operation change of the insertion portion 11, or the treatment operation of the endoscope.

Further, the video processor 30 is configured to determine the operation of the endoscope insertion portion as described above based on the insertion shape information or the like from the insertion shape detection device 40, and transmit the determination result to the lesion appearance identification unit (a lesion discovery operation determination unit 52A) in the image recording device 50, as operation stop information or operation change information of the endoscope insertion portion or as operation information about endoscopic treatment.

Note that in the present embodiment, each part of the video processor 30 may be configured as an individual electronic circuit, or may be configured as a circuit block in an integrated circuit such as an FPGA (field programmable gate array). In the present embodiment, for example, the video processor 30 may be configured with one or more processors (such as a CPU).

<Internal Configuration of the Image Recording Device 50 in the First Embodiment>

Next, the configuration of the image recording device 50 according to the present embodiment will be described in detail.

Figure 2:
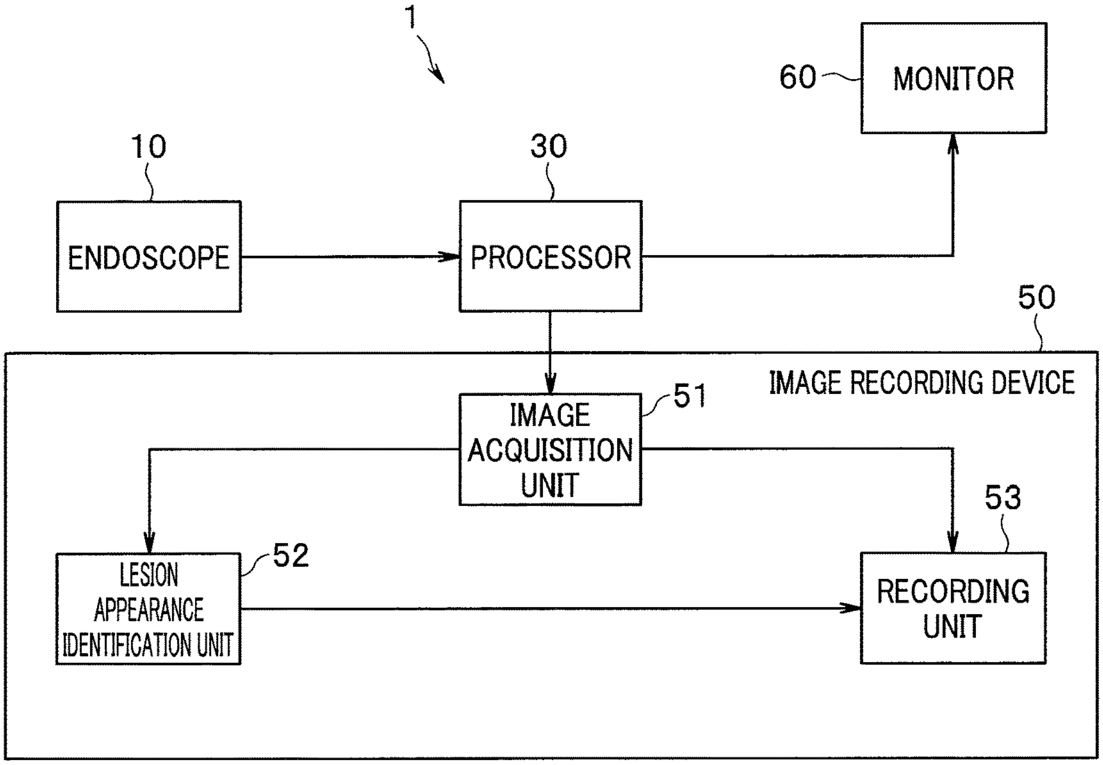
FIG. 2 is a block diagram illustrating a configuration of the image recording device of the first embodiment and a vicinity of the image recording device.
Figure 3:
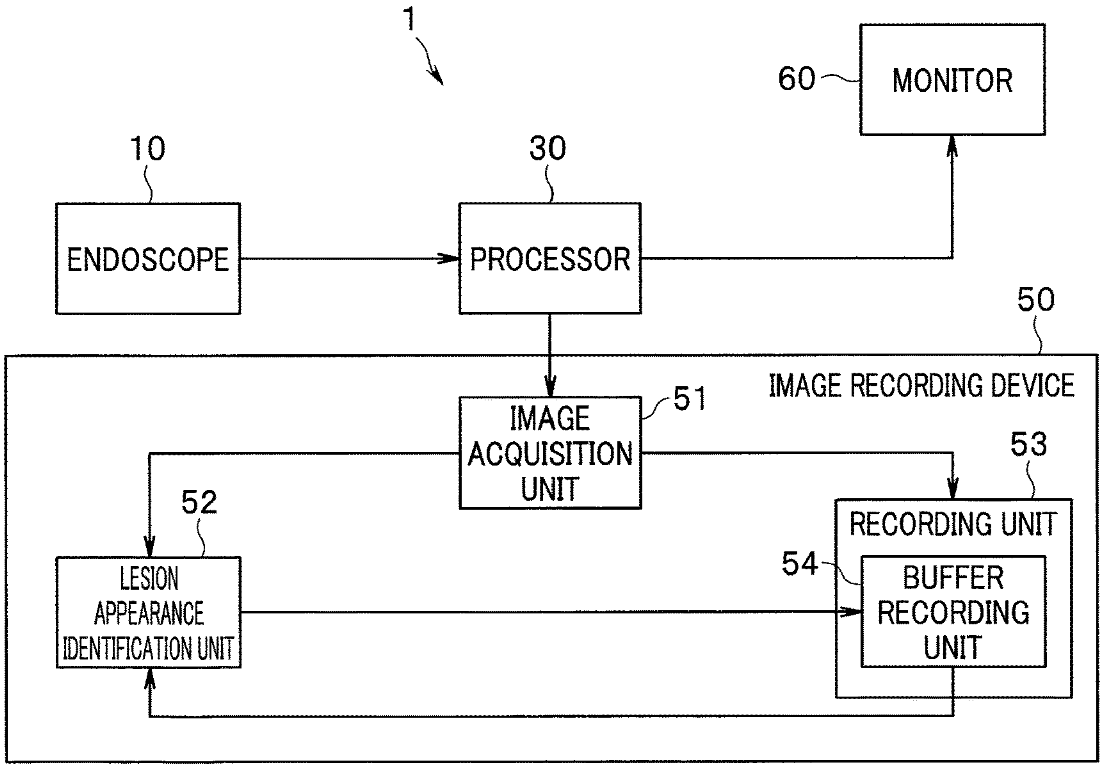
FIG. 3 is a block diagram illustrating a configuration of a recording unit in the image recording device of the first embodiment.
Figure 4:
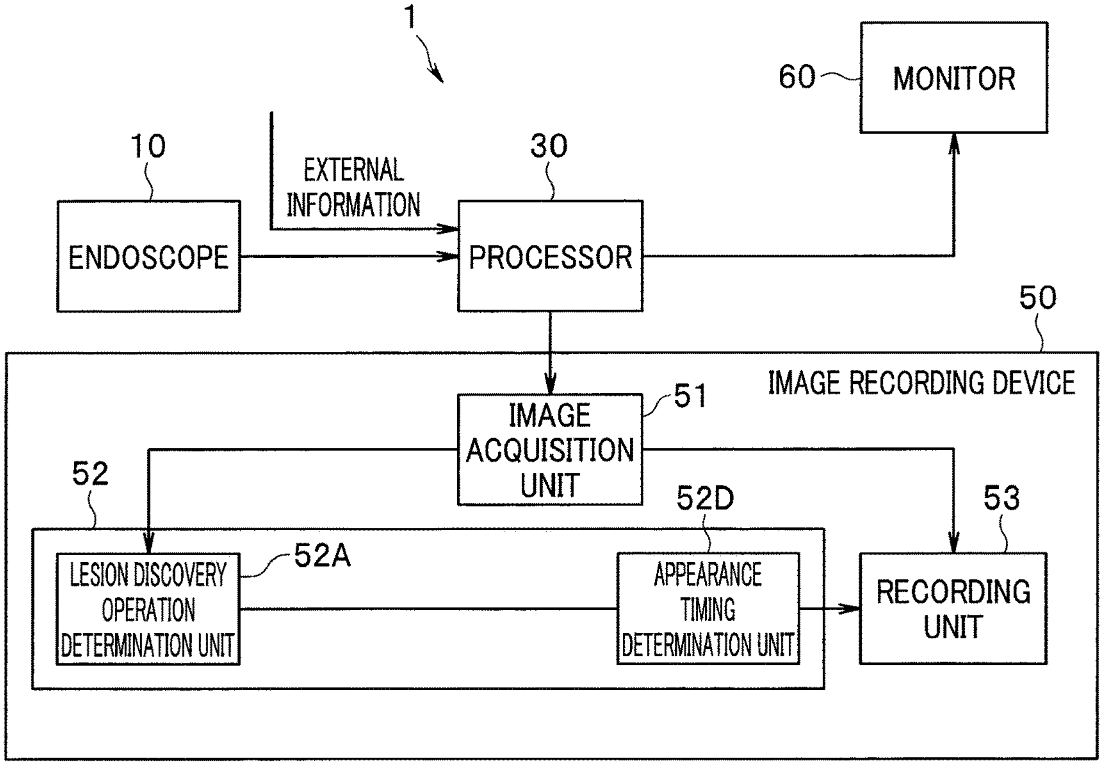
FIG. 4 is a block diagram showing a more specific configuration of the image recording device of the first embodiment.

FIG. 2 is a block diagram illustrating a configuration of the image recording device of the first embodiment and a vicinity of the image recording device, FIG. 3 is a block diagram illustrating a configuration of a recording unit in the image recording device of the first embodiment, and FIG. 4 is a block diagram showing a more specific configuration of the image recording device of the first embodiment.

Note that in the present embodiment, each part of the image recording device 50 may be configured as an electronic circuit, or may be configured as a circuit block in an integrated circuit such as an FPGA (field programmable gate array). In the present embodiment, for example, the image recording device 50 may be configured with one or more processors (such as a CPU).

As shown in FIG. 2, the image recording device 50 in the first embodiment includes an image acquisition unit 51 connected to the video processor 30 and configured to acquire time-series images of endoscopy, a lesion appearance identification unit 52 configured to identify, the appearance of a lesion from the time-series images acquired in the image acquisition unit 51, and a recording unit 53 configured to start recording of the time-series images from a time point when the appearance of the lesion is identified by the lesion appearance identification unit 52.

The image acquisition unit 51 is configured to acquire image pickup signals (image signals) outputted from the endoscope 10 and subjected to a predetermined image processing in the image processing unit of the video processor 30, and to transmit the image signals in the time series to the recording unit 53 and also to the lesion appearance identification unit 52.

After receiving the image signals in the time series, the lesion appearance identification unit 52 identifies appearance timing of the lesion based on corresponding time-series images, and transmits the appearance timing information to the recording unit 53.

The recording unit 53, which forms a memory, receives the time-series images from the image acquisition unit 51 as well as receiving the lesion appearance timing information from the lesion appearance identification unit 52, and starts recording of the time-series images according to the timing information, for example, recording of images in a lesion section including a time point immediately after the lesion appears in the time-series images of the endoscopy.

As described above, the recording unit 53 in the present embodiment performs recording of time-series images according to the timing information from the lesion appearance identification unit 52. In other words, the image recording device of the present embodiment makes it possible to easily create annotation data at timing when a lesion begins to appear in an important image in lesion detection using computer-aided detection/diagnosis (CADe).

Further, the recording unit 53 includes a teacher data creation unit configured to create teacher data for machine learning based on annotation data corresponding to a time-series image from the time-series images that is related to the lesion identified as appearing by the lesion appearance identification unit 52. The recording unit 53 also includes a learning model creation unit configured to create a learning model for recognition based on the teacher data created by the teacher data creation unit.

In this context, the learning model functions as a discriminator configured to identify a boundary of a feature portion on the endoscope image supposed to be a lesion based on the created teacher data.

Further, the recording unit 53 includes a recognition unit configured to perform predetermined recognition processing based on the learning model created by the learning model creation unit. More specifically, the recording unit 53 creates an algorithm for recognition processing by the recognition unit using, for example, a so-called deep learning technique. Then, the recognition algorithm is used to execute the recognition processing as appropriate.

Note that in the first embodiment, the recording unit 53 includes a buffer recording unit 54 as shown in FIG. 3. Further, the recording unit 53 records time-series images from the image acquisition unit 51 as appropriate, in parallel with recording of time-series images according to timing information from the lesion appearance identification unit 52.

Figure 9:
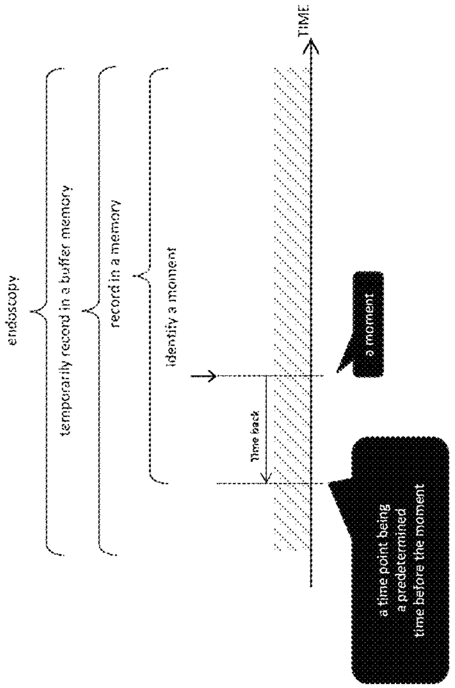
FIG. 9 illustrates an exemplary timing at which time-series images of endoscopy are recorded.

The buffer recording unit 54, which forms a buffer memory, allows recording of all the time-series images related to endoscopy which are outputted from the image acquisition unit 51, and in the present embodiment, further allows recording of time-series images at least from a time point a predetermined time before "a time point when a lesion appearance is identified" by the lesion appearance identification unit 52 to start (see FIG. 9).

Note that the lesion appearance identification unit 52 can retrieve the time-series images recorded in the buffer recording unit 54 and can identify a "lesion appearance" from the retrieved time-series images.

The recording unit 53 is capable of recording predetermined images of the time-series images recorded in the buffer recording unit 54, according to, for example, the appearance timing of the lesion identified by the lesion appearance identification unit 52 after the endoscopy is finished. The predetermined images are, for example, images in a section (lesion section) including a time point immediately after the lesion appears in the retrieved images.

With reference to FIG. 4, a specific configuration of the lesion appearance identification unit 52 in the image recording device 50 of the first embodiment will be described below.

Note that in FIG. 4, the recording unit 53 includes the buffer recording unit 54 as described above, although not specifically illustrated. Further, the recording unit 53 includes the above described teacher data creation unit, learning model creation unit, and recognition unit.

As shown in FIG. 4, the lesion appearance identification unit 52 in the first embodiment includes the lesion discovery operation determination unit 52A, and an appearance timing determination unit 52D configured to determine the timing of the appearance of a lesion.

The lesion discovery operation determination unit 52A detects an operation of discovering a lesion based on external information. In other words, the lesion discovery operation determination unit 52A serves as an operator notification information receiving unit configured to receive notification information about a lesion discovery operation performed by an operator and outputted from the video processor 30, and detect the discovery of the lesion based on the notification information.

Specifically, the lesion discovery operation determination unit 52A detects the discovery of the lesion based on voice information from the operator, predetermined image-recording operation information related to the operator, or predetermined still image generation operation information related to the operator, which is sent from the video processor 30.

As described above, the voice information from the operator, image-recording operation information and the like are sent from the video processor 30 to the lesion discovery operation determination unit 52A when the video processor 30 receives external information from, for example, the input device 70 or the scope switch 122.

On the other hand, the lesion discovery operation determination unit 52A detects the discovery of the lesion based on operation stop information or operation change information of an insertion portion of the endoscope, or operation information about endoscopic treatment, which is sent from the video processor 30.

As described above, such operation information about the endoscope is operation information about the insertion portion of the endoscope, which is determined by the video processor 30, for example, based on insertion shape information from the insertion shape detection device 40.

In the present embodiment, when the lesion discovery operation determination unit 52A detects an operation of discovering a lesion, the appearance timing determination unit 52D determines timing of the appearance of the lesion, and sends timing information based on the timing to the recording unit 53.

Specifically, when the appearance timing determination unit 52D detects an operation of lesion discovery by an operator (a voice of the operator, an image-recording operation, an operation of the endoscope insertion portion, or the like), the appearance timing determination unit 52D sends the timing information to the recording unit 53 such that endoscope images in the time series are recorded from a time point immediately after the detection or from a time point a predetermined time before the detection.

On the other hand, the recording unit 53 temporarily records time-series images from the image acquisition unit 51 in the buffer as appropriate, and records time-series images according to timing information from the lesion appearance identification unit 52, as described above.

Operation of the First Embodiment

Next, the operation of the image recording device of the first embodiment will be described.

First, the image acquisition unit 51 acquires time-series images of endoscopy sent from the video processor 30. Then, image signals in the time series are sent to the recording unit 53 and also to the lesion appearance identification unit 52.

The recording unit 53 records the time-series images received from the image acquisition unit 51 in the buffer recording unit 54 as appropriate, and on the other hand, waits for reception of timing information from the lesion appearance identification unit 52.

On the other hand, after receiving the image signals in the time series, the lesion appearance identification unit 52 identifies appearance timing of the lesion based on corresponding time-series images, by the above described lesion discovery operation determination unit 52A and appearance timing determination unit 52D, and sends the appearance timing information to the recording unit 53.

The recording unit 53 receives the time-series images from the image acquisition unit 51 and buffers the time-series images in the buffer recording unit 54, and when receiving the lesion appearance timing information from the lesion appearance identification unit 52, starts recording of the time-series images according to the timing information, for example, recording in a lesion section including a time point immediately after the lesion related to the time-series images of the endoscopy appears.

Thus, the recording unit 53 performs recording of time-series images according to the timing information from the lesion appearance identification unit 52, and in other words, creates annotation data at timing when a lesion begins to appear in an important image in lesion detection using computer-aided detection/diagnosis (CADe).

Subsequently, the recording unit 53 creates teacher data for machine learning based on the created annotation data, and further creates a learning model for recognition based on the teacher data.

Further, the recording unit 53 creates an algorithm for recognition processing based on the created learning model by a so-called deep learning technique or the like, and executes the recognition processing as appropriate.

Effect of the First Embodiment

In the image recording device of the first embodiment, when endoscopy is performed, notifications of the detection result and the differential result of a lesion are provided by a computer in real time, so that even inexperienced physicians can perform examination with quality not inferior to quality of veteran physicians.

Second Embodiment

Next, a second embodiment of the present invention will be described.

The image recording device of the second embodiment differs in the configuration of the lesion appearance identification unit 52 from the first embodiment. The image recording device of the first embodiment uses lesion appearance identification unit 52 to identify information about timing at which the recording unit 53 starts recording according to a lesion discovery operation by an operator or an operation of the endoscope insertion portion. In other words, the timing information is identified based on the operation of an operator in the first embodiment.

On the other hand, the image recording device of the second embodiment automatically detects the region of interest of a lesion from image signals of endoscopy images, calculates the lesion according to the detection of the region of interest and also identifies predetermined timing information according to the calculated lesion information, and further automatically records predetermined time-series images based on the timing information in the recording unit 53.

Since the other components are similar to the components of the first embodiment, only the difference from the first embodiment will be described here, and the description of the common parts will be omitted.

<Internal Configuration of the Image Recording Device 50 in the Second Embodiment>

Next, the configuration of the image recording device 50 according to the second embodiment will be described in detail.

Figure 5:
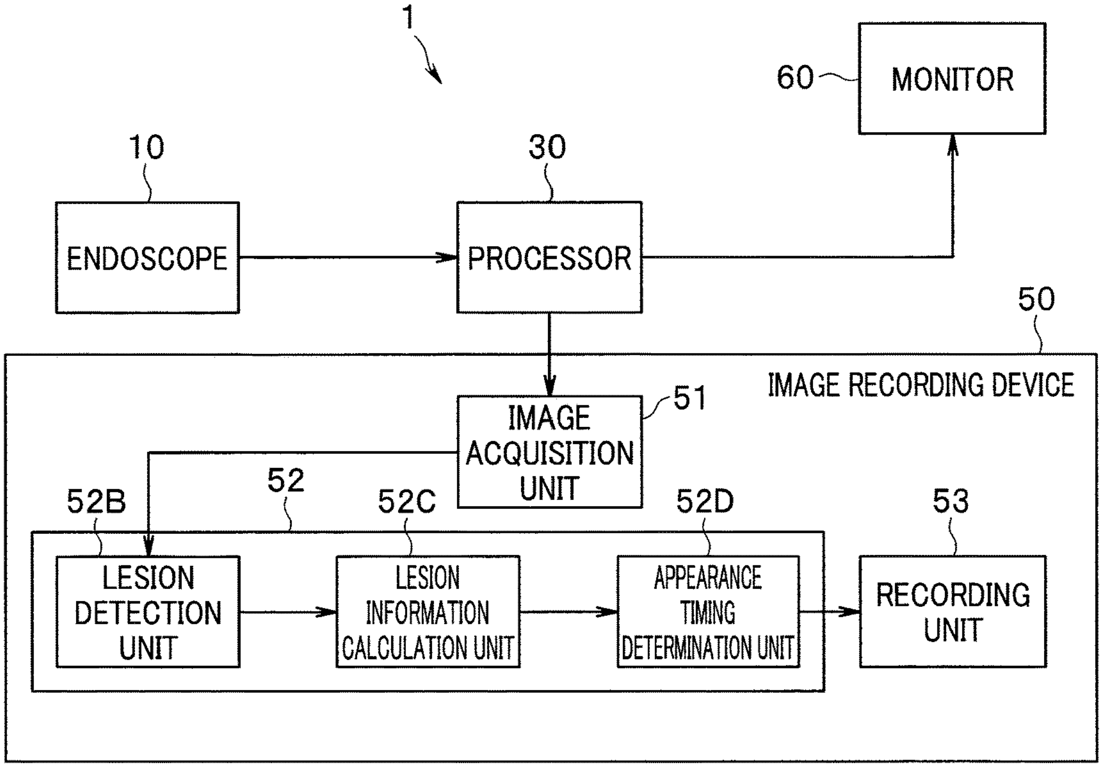
FIG. 5 is a block diagram illustrating a configuration of an image recording device according to a second embodiment of the present invention and a vicinity of the image recording device.

FIG. 5 is a block diagram illustrating a configuration of the image recording device according to the second embodiment of the present invention and a vicinity of the image recording device.

Note that also in FIG. 5, the recording unit 53 includes the buffer recording unit 54 as described above, although not specifically illustrated. Further, the recording unit 53 includes the above described teacher data creation unit, learning model creation unit, and recognition unit.

Also in the second embodiment, each part of the image recording device 50 may be configured as an electronic circuit, or may be configured as a circuit block in an integrated circuit such as an FPGA (field programmable gate array). In the present embodiment, for example, the image recording device 50 may be configured with one or more processors (such as a CPU).

As shown in FIG. 5, as in the first embodiment, the image recording device 50 in the second embodiment includes the image acquisition unit 51 connected to the video processor 30 and configured to acquire time-series images of endoscopy, the lesion appearance identification unit 52 configured to identify the appearance of a lesion from the time-series images acquired in the image acquisition unit 51, and the recording unit 53 configured to start recording of the time-series images from a time point when the appearance of the lesion is identified by the lesion appearance identification unit 52.

As in the first embodiment, the image acquisition unit 51 in the second embodiment is configured to acquire image pickup signals (image signals) outputted from the endoscope 10 and subjected to a predetermined image processing in the image processing unit of the video processor 30, and to transmit the image signals in the time series to the recording unit 53 and also to the lesion appearance identification unit 52.

After receiving the image signals in the time series, the lesion appearance identification unit 52 identifies appearance timing of the lesion based on corresponding time-series images, and transmits the appearance timing information to the recording unit 53. The recording unit 53 receives the time-series images from the image acquisition unit 51 as well as receiving the lesion appearance timing information from the lesion appearance identification unit 52, and starts recording of the time-series images according to the timing information, for example, recording in a lesion section including a time point immediately after the lesion related to the time-series images of the endoscopy appears.

Therefore, the second embodiment also makes it possible to easily create annotation data at timing when a lesion begins to appear in an important image in lesion detection using computer-aided detection/diagnosis (CADe).

The recording unit 53 in the second embodiment also includes a teacher data creation unit, a learning model creation unit, and a recognition unit as in the first embodiment, and executes recognition processing using a recognition algorithm created by a so-called deep learning technique or the like as appropriate.

Note that also in the second embodiment, the recording unit 53 includes the buffer recording unit 54 as shown in FIG. 3, and records time-series images from the image acquisition unit 51 as appropriate, in parallel with recording of time-series images according to timing information from the lesion appearance identification unit 52.

As shown in FIG. 5, in the second embodiment, the lesion appearance identification unit 52 includes a lesion detection unit 52B, a lesion information calculation unit 52C, and the appearance timing determination unit 52D.

The lesion detection unit 52B is configured to receive endoscopy image signals, which are time-series images acquired in the image acquisition unit 51, and apply known image processing to the image signals so as to detect a region of interest (ROI) as a "lesion".

The lesion information calculation unit 52C is configured to calculate the region of interest (ROI) information about the "lesion" based on the image data of the region of interest (ROI) detected by the lesion detection unit 52B.

Information about the "lesion" is, for example, time-series information about the region of interest (ROI) detected by the lesion detection unit 52B, position information about the region of interest (ROI), distance information about the region of interest (ROI), or size information about the region of interest (ROI).

Specifically, the lesion information calculation unit 52C compares the information on the time-series change, position, distance, or size of the region of interest (ROI) of the "lesion" detected by the lesion detection unit 52B with information obtained in advance, and if in a predetermined case, determines that the ROI indicates a "lesion".

In the second embodiment, w % ben the lesion detection unit 52B detects a predetermined region of interest (ROI), the appearance timing determination unit 52D determines timing of the appearance of the lesion according to information about "lesion" calculated by the lesion information calculation unit 52C, and sends timing information based on the timing to the recording unit 53.

Operation of the Second Embodiment

Next, the operation of the image recording device of the second embodiment will be described.

Also in the second embodiment, the image acquisition unit 51 first acquires time-series images of endoscopy sent from the video processor 30, and sends image signals in the time series to the recording unit 53 and also to the lesion appearance identification unit 52.

The recording unit 53 records the time-series images received from the image acquisition unit 51 in the buffer recording unit 54 as appropriate, and on the other hand, waits for reception of timing information from the lesion appearance identification unit 52.

On the other hand, the lesion detection unit 52B receives endoscopy image signals, which are the time-series images acquired in the image acquisition unit 51, and applies known image processing to the image signals so as to detect a region of interest (ROI) as a "lesion".

Subsequently, the lesion information calculation unit 52C calculates the "lesion" based on the image data of the region of interest (ROI) detected by the lesion detection unit 52B.

When the lesion detection unit 52B detects a predetermined region of interest (ROI), the appearance timing determination unit 52D determines timing of the appearance of the lesion according to information about "lesion" calculated by the lesion information calculation unit 52C, and sends timing information based on the timing to the recording unit 53.

The recording unit 53 receives the time-series images from the image acquisition unit 51 and buffers the time-series images in the buffer recording unit 54, and when receiving the lesion appearance timing information from the lesion appearance identification unit 52, starts recording of the time-series images according to the timing information, for example, recording in a lesion section including a time point immediately after the lesion related to the time-series images of the endoscopy appears.

Also in the second embodiment, the recording unit 53 performs recording of time-series images according to the timing information from the lesion appearance identification unit 52 (appearance timing determination unit 52D), and in other words, creates annotation data at timing when a lesion begins to appear in an important image in lesion detection using computer-aided detection/diagnosis (CADe).

Subsequently, the recording unit 53 creates teacher data for machine learning based on the created annotation data, and further creates a learning model for recognition based on the teacher data.

Further, the recording unit 53 creates an algorithm for recognition processing based on the created learning model by a so-called deep learning technique or the like, and executes the recognition processing as appropriate.

Effect of the Second Embodiment

The image recording device of the second embodiment automatically detects the region of interest of a lesion from image signals of endoscopy images, calculates the lesion according to the detection of the region of interest and also identifies predetermined timing information according to the calculated lesion information, and further automatically records predetermined time-series images based on the timing information, thereby allowing higher-quality examination.

Third Embodiment

Next, a third embodiment of the present invention will be described.

In an image recording device of the third embodiment, when a lesion detection unit detects a region of interest of a lesion, the image recording device performs predetermined lesion matching processing on image signals of time-series endoscopy images buffered in the buffer recording unit 54 in the recording unit 53, and identifies predetermined timing information according to the result of the matching.

Since the other components are similar to the components of the first embodiment, only the difference from the first embodiment will be described here, and the description of the common parts will be omitted.

<Internal Configuration of the Image Recording Device 50 in the Third Embodiment>

Next, the configuration of the image recording device 50 according to the third embodiment will be described in detail.

Figure 6:
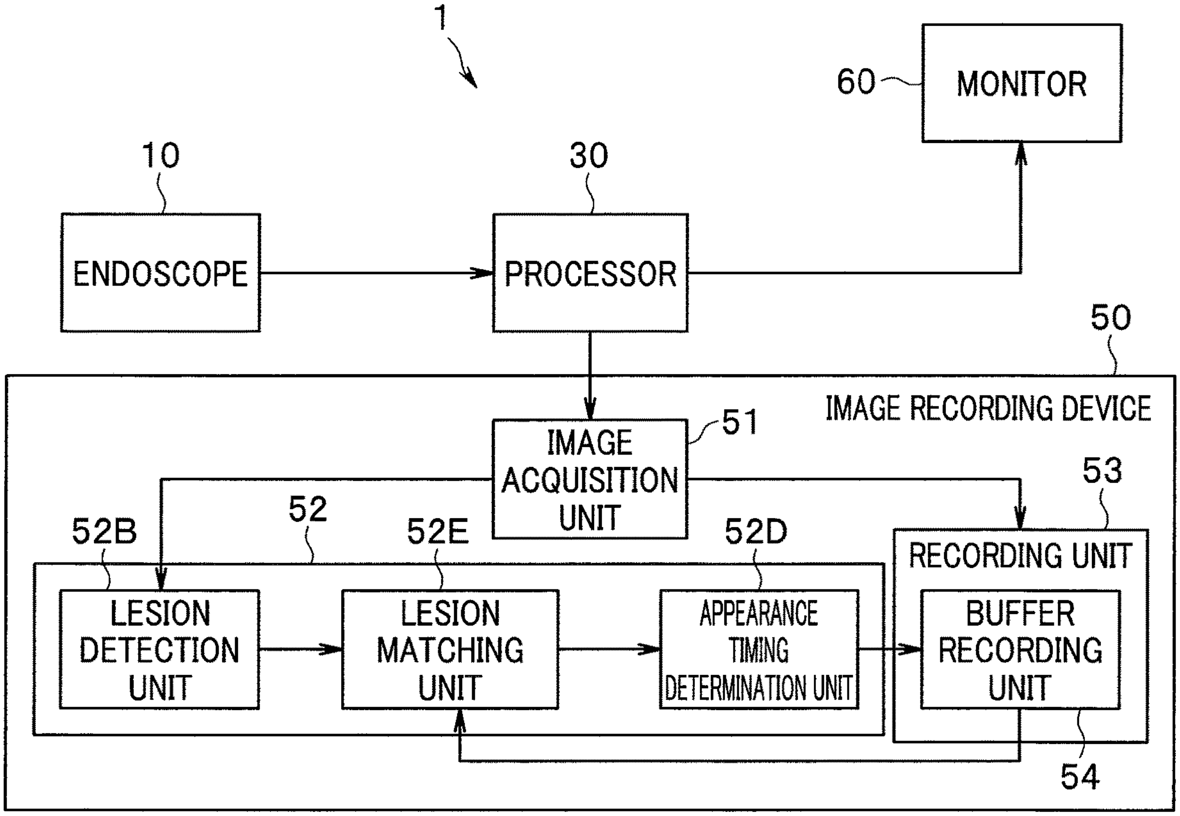
FIG. 6 is a block diagram illustrating a configuration of an image recording device according to a third embodiment of the present invention and a vicinity of the image recording device.

FIG. 6 is a block diagram illustrating a configuration of the image recording device according to the third embodiment of the present invention and a vicinity of the image recording device.

Also in the third embodiment, each part of the image recording device 50 may be configured as an electronic circuit, or may be configured as a circuit block in an integrated circuit such as an FPGA (field programmable gate array). In the present embodiment, for example, the image recording device 50 may be configured with one or more processors (such as a CPU).

As shown in FIG. 6, as in the first embodiment, the image recording device 50 in the third embodiment includes the image acquisition unit 51 connected to the video processor 30 and configured to acquire time-series images of endoscopy, the lesion appearance identification unit 52 configured to identify the appearance of a lesion from the time-series image acquired in the image acquisition unit 51, and the recording unit 53 configured to start recording of the time-series images from a time point when the appearance of the lesion is identified by the lesion appearance identification unit 52.

As shown in FIG. 6, in the third embodiment, the lesion appearance identification unit 52 includes the lesion detection unit 52B, a lesion matching unit 52E, and the appearance timing determination unit 52D.

As in the first embodiment, the image acquisition unit 51 in the third embodiment acquires image pickup signals (image signals) outputted from the endoscope 10 and subjected to a predetermined image processing in the image processing unit of the video processor 30, and transmits the image signals in the time series to the recording unit 53 (the buffer recording unit 54) and also to the lesion detection unit 52B in the lesion appearance identification unit 52.

Further, the buffer recording unit 54 in the recording unit 53 stores the endoscopy image signals in the time series received from the image acquisition unit 51 as a buffer.

As in the second embodiment, the lesion detection unit 52B is configured to receive endoscopy image signals, which are time-series images acquired in the image acquisition unit 51, and apply known image processing to the image signals so as to detect a region of interest (ROI) as a "lesion".

The lesion matching unit 52E is configured to, when the lesion detection unit 52B detects a region of interest (ROI), retrieve the endoscopy images buffered in the buffer recording unit 54 of the recording unit 53, and to perform matching between the retrieved images and the region of interest (ROI) detected by the lesion detection unit 52B.

In the third embodiment, when the lesion detection unit 52B detects a predetermined region of interest (ROI), the appearance timing determination unit 52D is configured to determine timing of the appearance of the lesion according to the matching result in the lesion matching unit 52E, and send timing information based on the timing to the recording unit 53.

Operation of the Third Embodiment

Next, the operation of the image recording device of the third embodiment will be described.

Also in the third embodiment, the image acquisition unit 51 first acquires time-series images of endoscopy sent from the video processor 30, and sends image signals in the time series to the buffer recording unit 54 of the recording unit 53 and also to the lesion appearance identification unit 52 (the lesion detection unit 52B).

The recording unit 53 records the time-series images received from the image acquisition unit 51 in the buffer recording unit 54 as appropriate, and on the other hand, waits for reception of timing information from the lesion appearance identification unit 52.

On the other hand, the lesion detection unit 52B receives endoscopy image signals, which are the time-series images acquired in the image acquisition unit 51, and applies known image processing to the image signals so as to detect a region of interest (ROI) as a "lesion".

When the lesion detection unit 52B detects a region of interest (ROI), the lesion matching unit 52E acquires the endoscopy images buffered in the buffer recording unit 54, and performs matching between the acquired images and the region of interest (ROI) detected by the lesion detection unit 52B.

Subsequently, the appearance timing determination unit 52D determines timing of the appearance of the lesion according to the matching result in the lesion matching unit 52E, and sends timing information based on the timing to the recording unit 53.

The recording unit 53 receives the time-series images from the image acquisition unit 51 and buffers the time-series images in the buffer recording unit 54, and when receiving the lesion appearance timing information from the lesion appearance identification unit 52, starts recording of the time-series images according to the timing information, for example, recording in a lesion section including a time point immediately after the lesion related to the time-series images of the endoscopy appears.

Also in the third embodiment, the recording unit 53 performs recording of time-series images according to the timing information from the lesion appearance identification unit 52 (the appearance timing determination unit 52D), and in other words, creates annotation data at timing when a lesion begins to appear in an important image in lesion detection using computer-aided detection/diagnosis (CADe).

Subsequently, the recording unit 53 creates teacher data for machine learning based on the created annotation data, and further creates a learning model for recognition based on the teacher data.

Further, the recording unit 53 creates an algorithm for recognition processing based on the created learning model by a so-called deep learning technique or the like, and executes the recognition processing as appropriate.

Effect of the Third Embodiment

In the image recording device in the third embodiment, when the lesion detection unit detects a region of interest of a lesion, the image recording device performs predetermined lesion matching processing on image signals of time-series endoscopy images buffered in the buffer recording unit 54 in the recording unit 53, and identifies predetermined timing information according to the result of the matching, thereby allowing higher-quality examination.

Fourth Embodiment

Next, a fourth embodiment of the present invention will be described.

Although the image recording device 50 is provided separately from the video processor 30 in the first to third embodiments, the function of the image recording device 50 is provided inside the video processor in the fourth embodiment.

Since the other components are similar to the components of the first embodiment, only the difference from the first embodiment will be described here, and the description of the common parts will be omitted.

Figure 7:
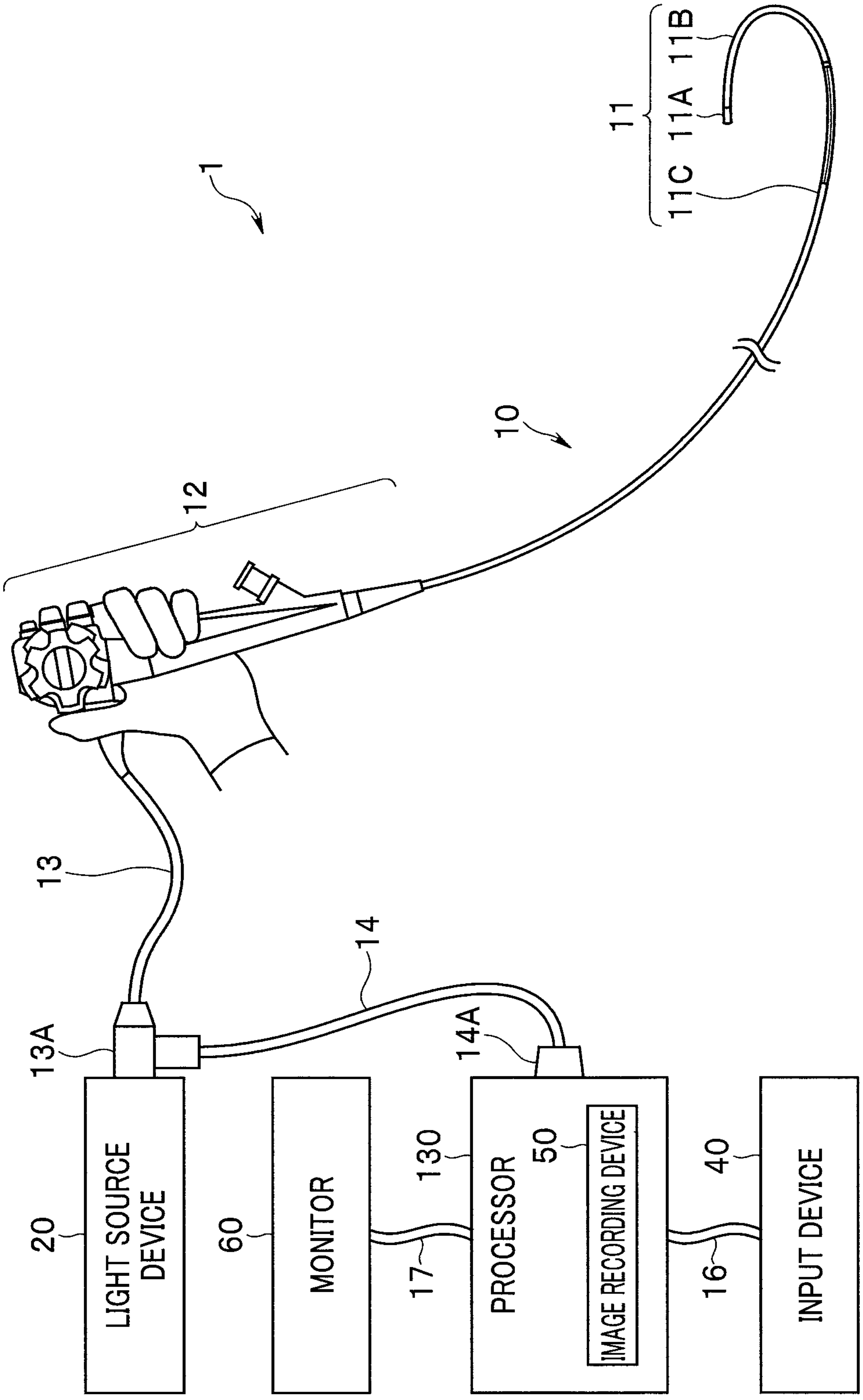
FIG. 7 is a block diagram showing a configuration of an endoscope system including an image recording device according to a fourth embodiment of the present invention.
Figure 8:
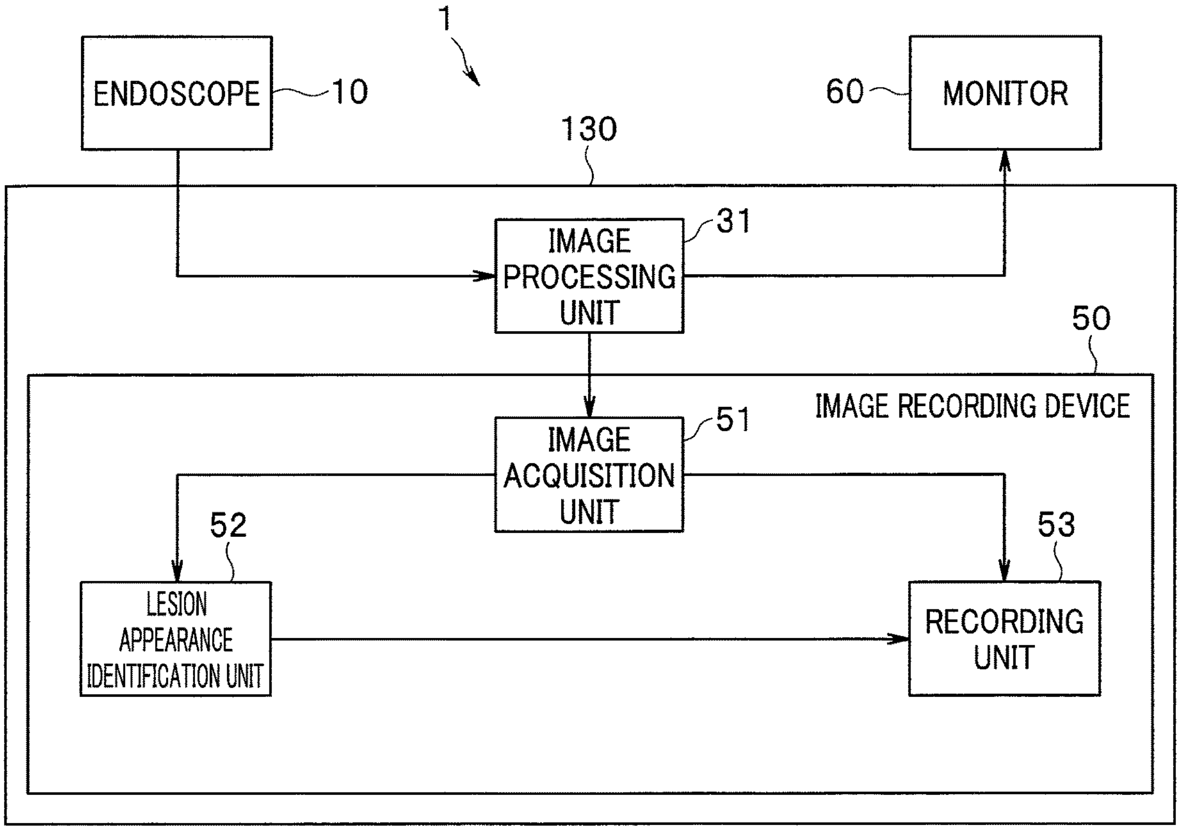
FIG. 8 is a block diagram illustrating a configuration of the image recording device of the fourth embodiment and a vicinity of the image recording device.

FIG. 7 is a block diagram showing a configuration of an endoscope system including an image recording device according to the fourth embodiment of the present invention, and FIG. 8 is a block diagram illustrating a configuration of the image recording device of the fourth embodiment and a vicinity of the image recording device.

As shown in FIG. 7, in the fourth embodiment, an image recording device 50 having a configuration equivalent to the image recording device 50 in the first embodiment is provided inside a video processor 130 including an image processing unit 31 which performs image processing similar to the image processing of the video processor 30 in the first embodiment.

The image recording device 50 in the fourth embodiment is similar to the image recording device 50 in the first embodiment except that the image recording device 50 in the fourth embodiment is integrated into the video processor, and also similar in operation and effect to the image recording device 50 in the first embodiment.

Also in the fourth embodiment, each part of the image recording device 50 may be configured as an electronic circuit, or may be configured as a circuit block in an integrated circuit such as an FPGA (field programmable gate array). In the present embodiment, for example, the image recording device 50 may be configured with one or more processors (such as a CPU).

The present invention is not limited to the above described embodiments, and various changes, modifications and the like may be made without departing from the gist of the present invention.

What is claimed is:

1. An image recording device comprising a processor, the processor being configured to:
- acquire time-series images of endoscopy;
- temporarily record the time-series images of the endoscopy in a buffer memory;
- retrieve the time-series images temporarily recorded in the buffer memory, and identify a moment of appearance of a lesion in the retrieved time-series images; and
- record, in a memory, the time-series images temporarily recorded in the buffer memory, the recording starting after a time point, the time point being a predetermined time before the moment of appearance of the lesion.

2. The image recording device according to claim 1, wherein from the time-series images temporarily recorded in the buffer memory, images in a section including a time point immediately after the lesion appears are recorded in the memory.

3. The image recording device according to claim 1, wherein the processor detects an operation of discovering the lesion based on external information.

4. The image recording device according to claim 3, wherein
- the processor sends timing information to the memory so as to record the time-series images of the endoscopy from the time point, and
- the time-series images are recorded according to the timing information in the memory.

5. The image recording device according to claim 3, wherein the processor detects the discovery of the lesion based on notification information about the lesion discovery operation by an operator.

6. The image recording device according to claim 5, wherein the processor detects the discovery of the lesion based on voice information from the operator, predetermined image-recording operation information related to the operator, or predetermined still image generation operation information related to the operator.

7. The image recording device according to claim 3, wherein the processor detects the discovery of the lesion based on information about an operation of an endoscope.

8. The image recording device according to claim 7, wherein the processor detects the discovery of the lesion based on operation stop information or operation change information of an insertion portion of the endoscope, or operation information about endoscopic treatment.

9. The image recording device according to claim 1, wherein the processor detects the lesion based on the retrieved time-series images.

10. The image recording device according to claim 9, wherein the processor further calculates information about the lesion based on the detected lesion.

11. The image recording device according to claim 10, wherein the processor calculates time-series information about the detected lesion.

12. The image recording device according to claim 10, wherein the processor calculates position information about the detected lesion.

13. The image recording device according to claim 10, wherein the processor calculates distance information about the detected lesion.

14. The image recording device according to claim 10, wherein the processor calculates size information about the detected lesion.

15. The image recording device according to claim 9, wherein the processor further performs matching processing of the lesion based on the detected lesion.

16. The image recording device according to claim 3, wherein the processor further determines the moment of appearance of the lesion.

17. The image recording device according to claim 1, wherein the processor:

creates teacher data for machine learning based on annotation data corresponding to a time-series image from the time-series images that is related to the lesion identified as appearing; and creates a learning model for recognition based on the created teacher data.

18. The image recording device according to claim 17, wherein the processor performs predetermined recognition processing based on the created learning model.

19. An image recording method comprising:

acquiring time-series images of endoscopy;

temporarily recording the time-series images of the endoscopy;

retrieving the temporarily recorded time-series images and identifying a moment of appearance of a lesion in the retrieved time-series images; and recording, in a memory, the time-series images temporarily recorded in the buffer memory, the recording starting after a time point, the time point being a predetermined time before the moment of appearance of the lesion.

20. A non-transitory computer-readable recording medium on which an image recording program is recorded, the recording medium causing a computer to:

execute the image recording program;

acquire time-series images of endoscopy;

temporarily record the time-series images of the endoscopy; retrieve the temporarily recorded time-series images and identify a moment of appearance of a lesion in the retrieved time-series images; and record, in a memory, the time-series images temporarily recorded in the buffer memory, the recording starting after a time point, the time point being a predetermined time before the moment of appearance of the lesion.

* * * * *